US012129226B2

(12) United States Patent
Guo et al.

(10) Patent No.: US 12,129,226 B2
(45) Date of Patent: Oct. 29, 2024

(54) PROCESS FOR ISOBUTANOL PRODUCTION FROM ETHANOL AND SYNGAS

(71) Applicants: UOP LLC, Des Plaines, IL (US); CHINA PETROLEUM & CHEMICAL CORPORATION, Beijing (CN)

(72) Inventors: Jinbiao Guo, Katy, TX (US); Richard Long, Katy, TX (US); Tian Ruan, Katy, TX (US)

(73) Assignees: China Petroleum & Chemical Corporation, Beijing (CN); UOP LLC, Des Plaines, IL (US)

( * ) Notice: Subject to any disclaimer, the term of this patent is extended or adjusted under 35 U.S.C. 154(b) by 458 days.

(21) Appl. No.: 17/597,863

(22) PCT Filed: Sep. 19, 2019

(86) PCT No.: PCT/US2019/051964
§ 371 (c)(1),
(2) Date: Jan. 31, 2022

(87) PCT Pub. No.: WO2021/054962
PCT Pub. Date: Mar. 25, 2021

(65) Prior Publication Data
US 2022/0281787 A1  Sep. 8, 2022

(51) Int. Cl.
*C07C 29/32* (2006.01)
*C07C 29/84* (2006.01)
(52) U.S. Cl.
CPC .............. *C07C 29/32* (2013.01); *C07C 29/84* (2013.01)

(58) Field of Classification Search
CPC ......... C07C 29/32; C07C 29/84; C07C 31/12; C07C 31/10
See application file for complete search history.

(56) References Cited

U.S. PATENT DOCUMENTS

| 5,300,695 A | 4/1994 | Radlowski |
| 5,508,246 A | 4/1996 | Apesteguia et al. |
| 5,559,275 A | 9/1996 | Barger |

(Continued)

FOREIGN PATENT DOCUMENTS

CN   101185895   5/2008

OTHER PUBLICATIONS

International Preliminary Report on Patentability from corresponding PCT application PCT/US2019/051964 mailed Mar. 31, 2022.

(Continued)

*Primary Examiner* — Jafar F Parsa
(74) *Attorney, Agent, or Firm* — Greer, Burns & Crain, Ltd.

(57) ABSTRACT

Processes for converting ethanol and syngas (CO and H2) to isobutanol are disclosed. Syngas and ethanol are reacted in the first reaction zone in the presence of a first heterogeneous catalyst to produce a first reactor effluent comprising a first mixture of alcohols. The first reactor effluent is reacted a second reaction zone in the presence of a second heterogeneous catalyst to produce a second reactor effluent comprising a second mixture of alcohols. The second reactor effluent is separated into an overhead gas stream and a liquid bottom stream. The liquid bottom stream is separated into at least a C1-2 stream, a C3 stream, and a C4+ stream. The isobutanol is recovered from the C4+ stream.

20 Claims, 1 Drawing Sheet

(56) References Cited

U.S. PATENT DOCUMENTS

| | | | |
|---|---|---|---|
| 5,703,133 | A | 12/1997 | Vanderspurt et al. |
| 5,811,602 | A | 9/1998 | Vanderspurt et al. |
| 5,939,352 | A | 8/1999 | Vanderspurt et al. |
| 8,354,563 | B2 | 1/2013 | Kharas |
| 9,227,895 | B2 | 1/2016 | Tirmizi et al. |
| 2013/0217935 | A1 | 8/2013 | Adam et al. |

OTHER PUBLICATIONS

International Search Report from corresponding PCT application PCT/US2019/051964, mailed Jun. 18, 2020.

Written Opinion from corresponding PCT application PCT/US2019/051964, mailed Jun. 18, 2020.

Air Products and Chemicals, Inc., Isobutanol from Syngas in a Three Phase System, Final Topical Report, Institute of Technical Chemistry and Petrol Chemistry, RWTH Aachen, Jan. 1993-Sep. 1999.

Li, Xiaoli, Effects of calcination temperature on structure-activity of K—ZrO$_2$/Cu/Al$_2$O$_3$ catalysts for ethanol and isobutanol synthesis from CO hydrogenation, Journal Article, Sep. 1, 2018, 199, 227, Fuel, Kidlington (abstract only).

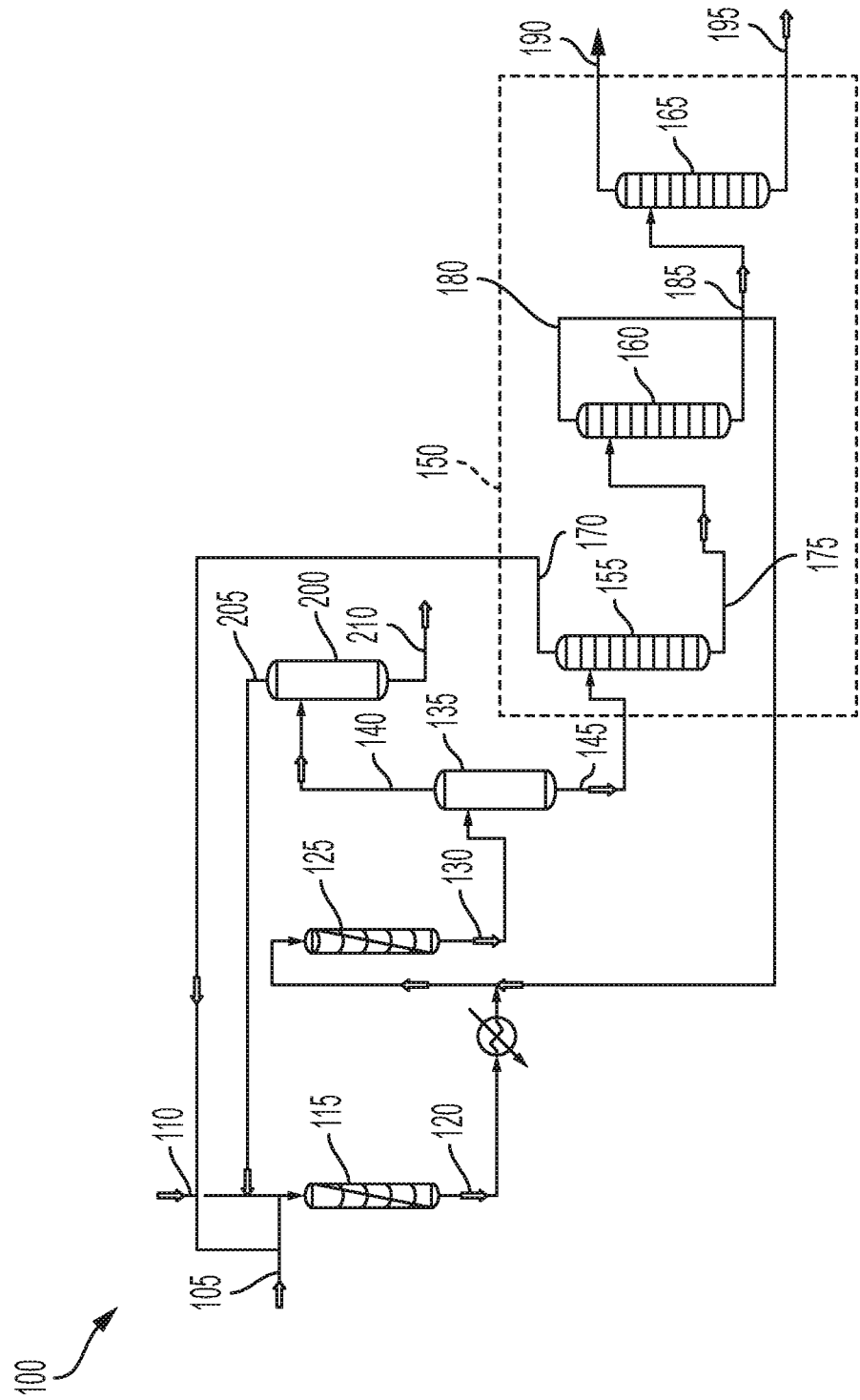

PROCESS FOR ISOBUTANOL PRODUCTION FROM ETHANOL AND SYNGAS

This application is a U.S. National Phase under 35 U.S.C. § 371 of International Application No. PCT/US2019/051964 filed Sep. 19. 2019, which is incorporated herein by reference in its entirety.

BACKGROUND

Ethanol is used primarily as a gasoline additive for improving combustion efficiency. Isobutanol can be considered as a second-generation biofuel. Isobutanol is an organic solvent and a feedstock in the manufacturing of isobutyl acetate and isobutyl esters. It can also be blended directly with gasoline to improve octane number and combustion efficiency or used as a neat alternative fuel. Isobutanol has relatively higher energy density, and lower volatility compared to ethanol. In addition, it does not readily absorb water from air, preventing the corrosion of engines and pipelines. It also has a higher octane number than ethanol, resulting in less knocking in engines.

Although isobutanol has many potential uses, its synthesis is currently limited. Isobutanol can be produced through carbonylation of propylene: a process involving reacting propylene with carbon monoxide and hydrogen to generate isobutyraldehyde and then hydrogenating the isobutyraldehyde to isobutanol. For example, U.S. Pat. No. 2,564,130 discloses a process for the manufacture of n-butanol and isobutanol from a mixture containing propylene, CO, and $H_2$ at 225-300° C. in the presence of a cobalt-containing catalyst. Although this carbonylation process is currently used for manufacturing butanol, it is not energy efficient due to the high energy needed for production of propylene and synthesis gas (syngas). It is also expensive due to the use of propylene. Further, when isobutanol is used as a gasoline additive, demand for it is expected to increase the demand for propylene significantly, making the process even more expensive.

Alternatively, synthesis of isobutanol directly from more abundant and less-expensive syngas has been investigated extensively. The syngas, containing carbon monoxide and hydrogen, is mainly produced from reforming or partial oxidation of natural gas and light hydrocarbons, or gasification of coal and biomass at high temperatures. It can also be produced from gasification of municipal solid waste. The carbon monoxide and hydrogen react at high temperatures and high pressures to produce methanol and isobutanol on alkali promoted ZnO and CuO—ZnO based catalysts, with methane and light hydrocarbons as main by-products. For example, U.S. Pat. No. 5,767,166 discloses an isobutanol synthesis process from syngas in one reactor on alkali promoted Zn—Cr oxide catalysts. A similar process is disclosed in CN Pat. Pub. No. 103,272,609 in which alkali and rare earth oxide promoted CuO—ZnO—$ZrO_2$ catalysts were used.

Although this direct isobutanol synthesis from syngas has been extensively investigated, it is often associated with poor isobutanol selectivity and productivity. During operation, lower temperature results in higher methanol selectivity, while higher temperature tends to produce more methane and light hydrocarbons. Consequently, high isobutanol selectivity and yield are difficult to achieve on the alkali promoted ZnO and CuO—ZnO catalysts.

Therefore, it would be desirable to have a process which can overcome the above obstacles and improve the isobutanol selectivity and productivity.

BRIEF DESCRIPTION OF THE DRAWINGS

The FIGURE illustrates one embodiment of the process of the present invention.

DETAILED DESCRIPTION

A new route to produce isobutanol using ethanol and syngas (CO and $H_2$) is disclosed. In the present process, ethanol, which is less expensive than propylene, reacts with CO and $H_2$ to generate isobutanol with $CO_2$ and/or water as byproducts. The first step is to convert ethanol and syngas to propanol. The second step is to convert propanol and syngas to isobutanol. This converts the current gasoline additive ethanol into a significantly more value-added isobutanol. The process is less expensive than the current process using propylene because ethanol is much less expensive than propylene. Furthermore, isobutanol has higher energy density than ethanol, and it does not readily absorb water from air, preventing the corrosion of engines and pipes.

Ethanol is conventionally produced from fermentation of sugar and starch, and ethylene hydration. Alternatively, other processes, such as Celanese's TCX process (syngas to ethanol via methanol intermediate), Yanchang Petroleum's coal to ethanol process, fermentation of syngas and conversion of biomass to ethanol, are being commercialized. With the rapid technology development, ethanol can be produced from many various feedstocks, such as traditional crop or fossil feedstocks, whole lignocellulosic biomass and waste materials. All of the development will diversify the feedstocks for ethanol production and allow the demand for ethanol not to compete with food. With enough ethanol supply, carbonylation of ethanol to isobutanol will add more values to the fuel additive, and reduce the isobutanol production cost as compared to conventional propylene carbonylation process.

The syngas can be produced from reforming or partial oxidation of natural gas and light hydrocarbons, or gasification of coal or biomass at high temperatures. It can also be produced from gasification of municipal solid waste. Therefore, this process can be applied to the processes of converting coal, natural gas, biomass, and/or waste to isobutanol.

The process involves the use of two (or more) reaction zones. In the first reaction zone, syngas and ethanol are reacted in the presence of a first heterogeneous catalyst at first reaction conditions including a first reaction temperature in the range of about 200° C. to about 500° C. to produce a first reactor effluent comprising a first mixture of alcohols. The syngas and ethanol are primarily converted to propanol under the reaction conditions in the first reaction zone, along with other alcohols, such as methanol and isobutanol. The first reactor effluent is sent to a second reaction zone and reacted in the presence of a second heterogeneous catalyst at second reaction conditions including a second reaction temperature in a range of about 250° C. to about 500° C. to produce a second reactor effluent comprising a second mixture of alcohols. The primary reaction in the second reaction zone is the conversion of propanol to isobutanol. The second reactor effluent is separated by condensation into an overhead gas stream and a liquid bottom stream. The liquid bottom stream is then separated into at least a $C_{1-2}$ alcohol stream comprising methanol or ethanol or both, a $C_3$ alcohol stream comprising propanol, and a $C_{4+}$ alcohol stream comprising isobutanol, using the technologies described below.

The liquid bottom stream can be separated using any suitable liquid separation process, including, but not limited to, an adsorption process, and a distillation process. The adsorption process may involve the use of a zeolite to adsorb a particular alcohol, followed by desorption of the alcohol at high temperature. The separation can also be achieved using a distillation process. The distillation process may involve the use of one or more distillation columns to separate the liquid bottom stream into the $C_{1-2}$ stream, the $C_3$ stream, and the $C_{4+}$ stream. The $C_{4+}$ stream may comprise isobutanol, and a small amount of n-butanol and higher alcohols which can then be separated from the isobutanol through distillation. The separation process may also be designed to provide one or more additional streams, such as or a $C_{5+}$ stream comprising alcohols having 5 or more carbon atoms, if desired.

The $C_{1-2}$ stream may be recycled back to the first reactor, and/or the $C_3$ stream may be recycled to the second reactor.

The overhead gas stream may be separated into a stream comprising $CO_2$, and a recycle synthesis gas stream comprising CO and $H_2$ through a conventional $CO_2$ separation process, such as adsorption by amine, alumina, zeolites, active carbon, selexol and rectisol as well as pressure swing and temperature swing. The recycle synthesis gas stream can be recycled to the first reactor.

At least one of the first catalyst or the second catalyst comprises Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof. Preferably, alkali oxide promoted Cu catalysts, alkali oxide promoted Zn catalysts, and alkali oxide promoted Pd catalysts are used. The first and second catalysts can be the same or different.

The first reaction temperature is typically in the range of about 200° C. to about 500° C., or about 250° C. to about 400° C. The second reaction temperature is typically in the range of about 250° C. to about 500° C., or about 270° C. to about 450° C.

The first and/or second reaction conditions may comprise at least one of: a pressure in a range of about 0.1 to about 30 MPa, or about 1 to about 20 MPa, or about 2 to about 15 MPa; a ratio of $H_2$ to CO in a range of about 5:1 to about 1:5, or about 3:1 to about 1:3, or about 2:1 to about 1:2; or a gas hourly space velocity in a range of about 100 to about 300,000 liters of gas per kg of catalyst per hr (L/kg-h), or about 500 to about 15,000 L/kg-h, or about 1000 to about 8,000 L/kg-h. In some embodiments, the first and/or second reactions conditions comprise a pressure in a range of about 0.1 to about 30 MPa; a ratio of $H_2$ to CO in a range of about 5:1 to about 1:5; and a gas hourly space velocity in a range of about 100 to about 300,000 L/kg-h. In some embodiments, the first and/or second reaction conditions include a pressure in a range of about 1 to about 20 MPa; a ratio of $H_2$ to CO in a range of about 3:1 to about 1:3; and a gas hourly space velocity in a range of about 500 to about 15,000 L/kg-h. In some embodiments, the first and/or second reaction conditions comprise a pressure in a range of 2 to about 15 MPa; a ratio of $H_2$ to CO in a range of about 2:1 to about 1:2; and a gas hourly space velocity in a range of about 1000 to about 8,000 L/kg-h.

The first reaction zone typically comprises about 0.5 and about 25 mol % ethanol, or about 1.0 and about 15 mol %, or about 1.5 and about 10 mol %.

One aspect of the invention is a method of making isobutanol. In one embodiment, the method comprises: reacting synthesis gas and ethanol in a first reaction zone in the presence of a first heterogeneous catalyst at first reaction conditions including a first reaction temperature in a range of about 200° C. to about 500° C. to produce a first reactor effluent comprising a first mixture of alcohols; reacting the first reactor effluent in a second reaction zone in the presence of a second heterogeneous catalyst at second reaction conditions including a second reaction temperature in a range of about 250° C. to about 500° C. to produce a second reactor effluent comprising a second mixture of alcohols; separating the second reactor effluent into an overhead gas stream and a liquid bottom stream; separating the liquid bottom stream into at least a $C_{1-2}$ stream comprising methanol or ethanol or both, a $C_3$ stream comprising propanol, and a $C_{4+}$ stream comprising isobutanol; and recovering the isobutanol.

In some embodiments, the method further comprises: recycling the $C_{1-2}$ stream to the first reaction zone. In some embodiments, the method further comprises: recycling the $C_3$ stream to the second reaction zone.

In some embodiments, the method further comprises: separating the overhead gas stream into a stream comprising $CO_2$, and a recycle synthesis gas stream comprising CO and $H_2$; and recycling the recycle synthesis gas stream to the first reactor.

In some embodiments, separating the liquid bottom stream comprises separating the liquid bottom stream using an adsorption process. In some embodiments, separating the liquid bottom stream comprising separating the liquid bottom stream using a distillation process. In some embodiments, the distillation process uses more than one distillation column.

In some embodiments, at least one of the first catalyst or the second catalyst comprises Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof.

In some embodiments, the first reaction zone contains between about 0.5 and about 25 mol % ethanol.

In some embodiments, the first reaction conditions or the second reaction conditions comprise at least one of: a pressure in a range of about 0.1 to about 30 MPa, a molar ratio of $H_2$ to CO in a range of about 5:1 to about 1:5, or a gas hourly space velocity in a range of about 100 to about 300,000 L/kg-h.

In some embodiments, the $C_{4+}$ stream further comprises n-butanol and higher alcohols, and wherein recovering the isobutanol comprises: separating the $C_{4+}$ stream into a stream comprising isobutanol and a stream comprising n-butanol and higher alcohols.

In some embodiments, the second reaction temperature is higher than the first reaction temperature.

In another aspect, the invention comprises a method of making isobutanol. In one embodiment the method comprises: reacting synthesis gas and ethanol in a first reaction zone in the presence of a first heterogeneous catalyst at first reaction conditions including a first reaction temperature in a range of about 200° C. to about 500° C. to produce a first reactor effluent comprising a first mixture of alcohols; reacting the first reactor effluent in a second reaction zone in the presence of a second heterogeneous catalyst at second reaction conditions including a second reaction temperature in a range of about 250° C. to about 500° C. to produce a second reactor effluent comprising a second mixture of alcohols; separating the second reactor effluent into an overhead gas stream and a liquid bottom stream; separating the liquid bottom stream into at least a $C_{1-2}$ stream comprising methanol or ethanol or both, a $C_3$ stream comprising propanol, and a $C_{4+}$ stream comprising isobutanol; recovering the isobutanol; recycling the $C_{1-2}$ stream to the first reaction zone; and recycling the $C_3$ stream to the second reaction zone.

In some embodiments, the method further comprises: separating the overhead gas stream into a stream comprising $CO_2$, and a recycle synthesis gas stream comprising CO and $H_2$; and recycling the recycle synthesis gas stream to the first reactor.

In some embodiments, separating the liquid bottom stream comprises separating the liquid bottom stream using an adsorption process. In some embodiments, separating the liquid bottom stream comprising separating the liquid bottom stream using a distillation process. In some embodiments, the distillation process uses more than one distillation column.

In some embodiments, at least one of the first catalyst or the second catalyst comprises Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof.

In some embodiments, the first reaction zone comprises between about 0.5 and about 25 mol % ethanol. The rest of the feed is a mixed gas which contains CO and $H_2$.

In some embodiments, the first reaction conditions or the second reaction conditions comprise at least one of: a pressure in a range of about 0.1 to about 30 MPa, a molar ratio of $H_2$ to CO in a range of about 5:1 to about 1:5, or a gas hourly space velocity in a range of about 100 to about 300,000 L/kg-h.

In some embodiments, the $C_{4+}$ stream further comprises n-butanol and higher alcohols, and wherein recovering the isobutanol comprises: separating the $C_{4+}$ stream into a stream comprising isobutanol and a stream comprising n-butanol and higher alcohols.

The FIGURE illustrates one embodiment of the process 100 of the present invention. An ethanol feed stream 105 and a syngas feed stream 110 are introduced into the first reaction zone 115. The syngas feed stream 110 comprises CO, $H_2$, and up to about 1-10% $CO_2$. The first reaction zone comprises about 0.5 to 25 mol % ethanol, with the remainder being syngas. The first reaction zone contains a first heterogeneous catalyst comprising Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof. The temperature in the first reaction zone 115 is generally in the range of about 200° C. to about 500° C. Other typical reaction conditions for the first reaction zone 115 include one or more of: a pressure in a range of about 0.1 to about 30 MPa, a molar ratio of $H_2$ to CO in a range of about 5:1 to about 1:5, or a gas hourly space velocity in a range of about 100 to about 300,000 L/kg-h. The ethanol and syngas react in the first reaction zone 115 to produce a mixture of alcohols. One of the primary reactions in the first reaction zone 115 is the conversion of ethanol to propanol.

The first reactor effluent 120 comprising the first mixture of alcohols is sent to the second reaction zone 125. The second reaction zone 125 is operated at a second reaction temperature in the range of about 250° C. to about 500° C. This results in the primary reaction in the second reaction zone being the conversion of propanol to isobutanol. The second reaction zone 125 contains a second heterogeneous catalyst comprising Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof. Other typical reaction conditions for the second reaction zone 125 include one or more of: a pressure in a range of about 0.1 to about 30 MPa, a molar ratio of $H_2$ to CO in a range of about 5:1 to about 1:5, or a gas hourly space velocity in a range of about 100 to about 300,000 L/kg-h.

The effluent 130 from the second reaction zone 125 which comprises a mixture of alcohols is sent to a gas-liquid separator 135 where it is separated into an overhead gas stream 140 and a liquid bottom stream 145.

The liquid bottom stream 145 from separator 135 is sent to a separation zone 150. As illustrated, the separation comprises three distillation columns 155, 160, 165. The liquid bottom stream 145 is sent to the first distillation column 155 where it is separated into an overhead stream 170 and a bottom stream 175. The overhead stream 170 from the first distillation column 155 which comprises methanol, ethanol, or both is recycled to the first reaction zone 115.

The bottom stream 175 from the first distillation column 155 comprises alcohols having 3 or more carbon atoms. The bottom stream 175 is sent to the second distillation column 160 where it is separated into overhead stream 180 and bottom stream 185. The overhead stream 180 from the second distillation column 160 comprises propanol and is recycled to the second reaction zone 125.

The bottom stream 185 from the second distillation column 160 comprises alcohols having 4 or more carbon atoms. The bottom stream 185 is sent to the third distillation column 165 where it is separated into overhead stream 190 and bottom stream 195. The overhead stream 190 from the third distillation column 165 comprises isobutanol. The isobutanol can be recovered from the overhead stream 190.

The bottom stream 195 from the third distillation column 165 comprises n-butanol and higher alcohols, which can be collected as byproduct. The long chain alcohols byproduct could be further processed to solvents, chemicals or fuel.

Although the separation zone 150 is illustrated as including three distillation columns, other separation zones are possible. For example, there could be a single distillation with multiple sidedraw streams, or there are more than three distillation columns with at least one for $C_{5+}$ alcohols separation.

The overhead gas stream 140 from the separator 135 comprises $CO_2$, CO, and $H_2$. The overhead gas stream 140 from separator 135 is sent to a separator 200 where it is separated into an overhead stream 205 and a bottom stream 210. The overhead stream 205 from separator 200 which comprises CO and $H_2$ is recycled to the first reaction zone 115. The bottom stream 210 from separator 200 comprises $CO_2$ which is trapped and recycled or released. The separator 200 could be a conventional $CO_2$ separator, such as an adsorption bed by amine, alumina, zeolites, active carbon, Selexol® and Rectisol®, membrane, as well as pressure swing reactor.

EXAMPLES

Example 1

A $CuO—ZnO—Al_2O_3$ catalyst was prepared with conventional co-precipitation method. Next $K_2O$ was impregnated on the surface with incipient wetness impregnation. The catalyst had a composition of 3% $K_2O$, 62% CuO, 25% ZnO and 10% $Al_2O_3$. The catalyst was tested in a tubular reactor under the conditions of 370° C., 100 atm, 45% $H_2$, 45% CO, 10% $N_2$, and gas hourly space velocity of 4,000 ml/g-h. 34% CO conversion was achieved. The yields of methanol, ethanol, propanol and isobutanol were 114, 9, 28 and 27 g/kg-h, respectively.

Example 2

The same $K_2O/CuO$—$ZnO$—$Al_2O_3$ catalyst in Example 1 was tested in a tubular reactor under the conditions of 340° C., 100 atm, 43% $H_2$, 43% CO, 5% $C_2H_5OH$, 9% $N_2$, and gas hourly space velocity of 4,000 ml/g-h. 33% CO conversion and 83% ethanol conversion were achieved. The yields of methanol, propanol and isobutanol were 201, 173 and 24 g/kg-h, respectively. It is clear that ethanol was mainly converted to propanol (173 g/kg-h) by reacting with syngas.

Example 3

The same $K_2O/CuO$—$ZnO$—$Al_2O_3$ catalyst in Example 1 was tested in a tubular reactor under the conditions of 370° C., 100 atm, 44% $H_2$, 44% CO, 3% $C_3H_7OH$, 9% $N_2$, and gas hourly space velocity of 4,000 ml/g-h. 34% CO conversion and 63% propanol conversion were achieved. The yields of methanol, ethanol and isobutanol were 94, 0 and 102 g/kg-h, respectively. It suggests that propanol was converted to isobutanol by reacting with syngas. The isobutanol yield was increased from 27 g/kg-h with syngas only (Example 1) to 102 g/kg-h with propanol and syngas (Example 3).

Example 4

A $Cs_2O$ doped $CuO$—$ZnO$—$Al_2O_3$ catalyst was tested in a tubular reactor under the conditions of 340° C., 100 atm, 44% $H_2$, 44% CO, 3% $C_3H_7OH$, 9% $N_2$, and gas hourly space velocity of 4,000 ml/g-h. The catalyst had a composition of 3% $Cs_2O$, 62% CuO, 25% ZnO and 10% $Al_2O_3$. 48% CO conversion and 82% propanol conversion were achieved. The yields of methanol, ethanol and isobutanol were 155, 15 and 122 g/kg-h, respectively. It suggests that propanol was converted to isobutanol by reacting with syngas on the catalyst.

As used herein, the term "stream" can include various alcohols, and optionally other substances, such as gases, e.g., hydrogen, or impurities, such as metals, and sulfur and nitrogen compounds. Moreover, the alcohol molecules may be abbreviated $C_1$, $C_2$, $C_3$ . . . Cn where "n" represents the number of carbon atoms in the one or more alcohol molecules. Furthermore, a superscript "+" or "−" may be used with an abbreviated one or more hydrocarbons notation, e.g., $C_{3+}$ or $C_{3-}$, which is inclusive of the abbreviated one or more alcohols. As an example, the abbreviation "$C_{3+}$" means one or more alcohol molecules of three and/or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, "about" is understood to mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of making isobutanol comprising:
reacting synthesis gas and ethanol in a first reaction zone in the presence of a first heterogeneous catalyst at first reaction conditions including a first reaction temperature in a range of about 200° C. to about 500° C. to produce a first reactor effluent comprising a first mixture of alcohols;
reacting the first reactor effluent in a second reaction zone in the presence of a second heterogeneous catalyst at second reaction conditions including a second reaction temperature in a range of about 250° C. to about 500° C. to produce a second reactor effluent comprising a second mixture of alcohols;
separating the second reactor effluent into an overhead gas stream and a liquid bottom stream;
separating the liquid bottom stream into at least a $C_{1-2}$ stream comprising methanol or ethanol or both, a $C_3$ stream comprising propanol, and a $C_{4+}$ stream comprising isobutanol; and
recovering the isobutanol.

2. The method of claim 1 further comprising:
recycling the $C_{1-2}$ stream to the first reaction zone.

3. The method of claim 1 further comprising:
recycling the $C_3$ stream to the second reaction zone.

4. The method of claim 1 further comprising:
separating the overhead gas stream into a stream comprising $CO_2$, and a recycle synthesis gas stream comprising CO and $H_2$; and
recycling the recycle synthesis gas stream to the first reactor.

5. The method of claim 1 wherein separating the liquid bottom stream comprising separating the liquid bottom stream using an adsorption process.

6. The method of claim 1 wherein separating the liquid bottom stream comprising separating the liquid bottom stream using a distillation process.

7. The method of claim 6 wherein the distillation process uses more than one distillation column.

8. The method of claim 1 wherein at least one of the first catalyst or the second catalyst comprises Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof.

9. The method of claim 1 wherein the first reaction zone contains between about 0.5 and about 25 mol % ethanol.

10. The method of claim 1 wherein the first reaction conditions or the second reaction conditions comprise at least one of: a pressure in a range of about 0.1 to about 30 MPa, a molar ratio of $H_2$ to CO in a range of about 5:1 to about 1:5, or a gas hourly space velocity in a range of about 100 to about 300,000 L/kg-h.

11. The method of claim 1 wherein the $C_{4+}$ stream further comprises n-butanol and higher alcohols, and wherein recovering the isobutanol comprises:

separating the $C_{4+}$ stream into a stream comprising isobutanol and a stream comprising n-butanol and higher alcohols.

12. The method of claim 1 wherein the second reaction temperature is higher than the first reaction temperature.

13. A method of making isobutanol comprising:
reacting synthesis gas and ethanol in a first reaction zone in the presence of a first heterogeneous catalyst at first reaction conditions including a first reaction temperature in a range of about 200° C. to about 500° C. to produce a first reactor effluent comprising a first mixture of alcohols;
reacting the first reactor effluent in a second reaction zone in the presence of a second heterogeneous catalyst at second reaction conditions including a second reaction temperature in a range of about 250° C. to about 500° C. to produce a second reactor effluent comprising a second mixture of alcohols;
separating the second reactor effluent into an overhead gas stream and a liquid bottom stream;
separating the liquid bottom stream into at least a $C_{1-2}$ stream comprising methanol or ethanol or both, a $C_3$ stream comprising propanol, and a $C_{4+}$ stream comprising isobutanol;
recovering the isobutanol ;
recycling the $C_{1-2}$ stream to the first reaction zone; and
recycling the $C_3$ stream to the second reaction zone.

14. The method of claim 13 further comprising: separating the overhead gas stream into a stream comprising $CO_2$, and a recycle synthesis gas stream comprising CO and $H_2$; and recycling the recycle synthesis gas stream to the first reactor.

15. The method of claim 13 wherein separating the liquid bottom stream comprising separating the liquid bottom stream using an adsorption process or a distillation process.

16. The method of claim 15 wherein the distillation process uses more than one distillation column.

17. The method of claim 13 wherein at least one of the first catalyst or the second catalyst comprises Cu, Ag, Au, Zn, Rh, Pd, Pt, Cr, Mn, Fe, Co, Ni, Al, Si, Zr, Ti, alkali oxides and salts, alkaline earth oxides and salts, rare earth oxides and salts, or combinations thereof.

18. The method of claim 13 wherein the first reaction zone comprises between about 0.5 and about 25 mol % ethanol.

19. The method of claim 13 wherein the first reaction conditions or the second reaction conditions comprise at least one of: a pressure in a range of about 0.1 to about 30 MPa, a molar ratio of $H_2$ to CO in a range of about 5:1 to about 1:5, or a gas hourly space velocity in a range of about 100 to about 300,000 L/kg-h.

20. The method of claim 13 wherein the $C_{4+}$ stream further comprises n-butanol and higher alcohols, and wherein recovering the isobutanol comprises:
separating the $C_{4+}$ stream into a stream comprising isobutanol and a stream comprising n-butanol and higher alcohols.

* * * * *